(12) United States Patent
Degner et al.

(10) Patent No.: US 10,408,745 B2
(45) Date of Patent: Sep. 10, 2019

(54) METHOD AND DEVICE FOR MEASURING THE CONCENTRATION OF SUBSTANCES IN GASEOUS OR FLUID MEDIA THROUGH OPTICAL SPECTROSCOPY USING BROADBAND LIGHT SOURCES

(71) Applicant: bluepoint MEDICAL GmbH & Co., KG, Selmsdorf (DE)

(72) Inventors: Martin Degner, Kröpelin (DE); Hartmut Ewald, Rostock (DE); Nils Damaschke, Bargeshagen (DE); Elfred Lewis, O'Brians's Bridge (IE)

(73) Assignee: BLUEPOINT MEDICAL GMBH & CO. KG., Selmsdorf (DE)

( * ) Notice: Subject to any disclaimer, the term of this patent is extended or adjusted under 35 U.S.C. 154(b) by 333 days.

(21) Appl. No.: 15/226,614

(22) Filed: Aug. 2, 2016

(65) Prior Publication Data

US 2016/0341660 A1 Nov. 24, 2016

Related U.S. Application Data

(63) Continuation of application No. 13/141,380, filed as application No. PCT/EP2009/066840 on Dec. 10, 2009, now abandoned.

(30) Foreign Application Priority Data

Dec. 22, 2008 (DE) .................. 10 2008 064 173

(51) Int. Cl.
*G01N 21/31* (2006.01)
*G01N 21/33* (2006.01)
(Continued)

(52) U.S. Cl.
CPC ............... *G01N 21/33* (2013.01); *G01J 3/02* (2013.01); *G01J 3/0297* (2013.01); *G01J 3/42* (2013.01);
(Continued)

(58) Field of Classification Search
None
See application file for complete search history.

(56) References Cited

U.S. PATENT DOCUMENTS

| 3,811,776 A | 5/1974 | Blau |
| 5,012,809 A | 5/1991 | Schulze |

(Continued)

FOREIGN PATENT DOCUMENTS

| EP | 0 145 877 A2 | 6/1985 |
| EP | 0 656 535 A1 | 6/1995 |

(Continued)

OTHER PUBLICATIONS

Written Opinion of the International Searching Authority for PCT/EP2009/066840, dated Apr. 6, 2010.
(Continued)

*Primary Examiner* — Neil N Turk
(74) *Attorney, Agent, or Firm* — Curatolo Sidoti Co., LPA; Joseph G. Curatolo; Salvatore A. Sidoti

(57) ABSTRACT

A method of referencing in optical absorption spectroscopy using broadband light sources for determining the concentration of substances in gaseous or fluid media through and to a device for measuring the concentration of substances in gaseous or fluid media within the measurement path of a measurement cell using absorption spectroscopy of light emitted from broadband light sources via light guiding optics.

13 Claims, 4 Drawing Sheets

Figure 1:
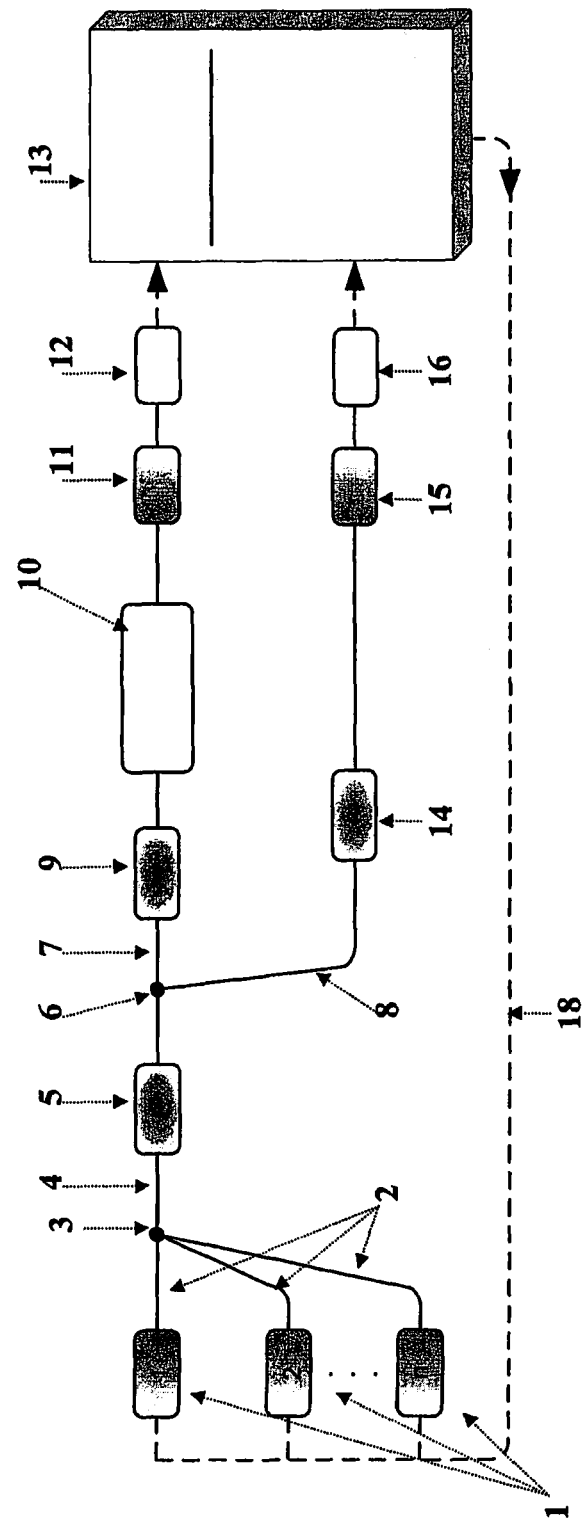

(51) Int. Cl.
*G01J 3/02* (2006.01)
*G01N 21/27* (2006.01)
*G01J 3/42* (2006.01)
*G01N 21/3504* (2014.01)
*G01N 21/03* (2006.01)

(52) U.S. Cl.
CPC ....... *G01N 21/0303* (2013.01); *G01N 21/274* (2013.01); *G01N 21/31* (2013.01); *G01N 21/3504* (2013.01); *G01N 2021/0307* (2013.01); *G01N 2201/062* (2013.01); *G01N 2201/0631* (2013.01); *G01N 2201/0668* (2013.01); *G01N 2201/08* (2013.01)

(56) References Cited

U.S. PATENT DOCUMENTS

| | | | |
|---|---|---|---|
| 5,173,749 A | | 12/1992 | Tell et al. |
| 5,303,036 A | | 4/1994 | McLachlan et al. |
| 5,445,964 A | * | 8/1995 | Lee .................. G01N 21/39 250/343 |
| 5,528,040 A | * | 6/1996 | Lehmann ................ G01J 3/42 250/343 |
| 5,559,333 A | | 9/1996 | Araya et al. |
| 5,572,031 A | * | 11/1996 | Cooper ............ G01D 3/0365 250/343 |
| 5,693,945 A | | 12/1997 | Akiyama et al. |
| 5,818,598 A | * | 10/1998 | Kebabian .......... G01N 21/3518 356/434 |
| 7,170,607 B2 | | 1/2007 | Yoon et al. |
| 7,323,687 B2 | | 1/2008 | Tomoaki et al. |
| 2004/0179200 A1 | | 9/2004 | Yoon et al. |

FOREIGN PATENT DOCUMENTS

| | | |
|---|---|---|
| GB | 2 233 087 A | 1/1991 |
| WO | WO 93/06458 | 4/1993 |
| WO | 2005/108939 A1 | 11/2005 |

OTHER PUBLICATIONS

International Search Report for PCT/EP2009/066840, dated Apr. 6, 2010.
International Preliminary Report on Patentability for PCT/EP2009/066840, dated Jun. 29, 2011.
Lewis, Elfed., et al., "Monitoring of Environmentally Hazardous Exhaust Emissions from Cars Using Optical Fibre Sensors", Embedded Computer Systems: Architectures, Modeling, and Simulation, Jul. 21, 2008, pp. 238-247, XP019092443.
Degner, M., et al., "Real Time Exhaust Gas Sensor with High Resolution for Onboard Sensing of Harmful Components", Sensors, 2008 IEEE, Oct. 26, 2008, pp. 973-976, XP031375242.
Degner, M., et al., "Low Cost Sensor for Online Detection of Harmful Diesel Combustion Gases in the UV-VIS Region", Proceedings of the SPIE—The International Society for Optical Engineering, Jan. 1, 2006, vol. 6198, pp. 619806-1 to 619806-11, XP007912266.
GB 1111225.7—Great Britain Search Report, dated Sep. 25, 2012.
European Patent Application No. 15192390.1-1554—European Search Report, dated Mar. 18, 2016.

* cited by examiner

METHOD AND DEVICE FOR MEASURING THE CONCENTRATION OF SUBSTANCES IN GASEOUS OR FLUID MEDIA THROUGH OPTICAL SPECTROSCOPY USING BROADBAND LIGHT SOURCES

The present application is a continuation of co-pending U.S. Ser. No. 13/141,380, having a 35 U.S.C. 371 date of Sep. 21, 2011, which is a national phase application of International Patent Application PCT/EP2009/066840, filed Dec. 10, 2009, which claims priority from German Patent Application Serial No. 10 2008 064 173.1, filed Dec. 22, 2008.

The invention relates to a method of referencing in the optical absorption spectroscopy using broadband light sources for determining the concentration of substance in gaseous or fluid media through and to a device for measuring the concentration of substance in gaseous or fluid media within the measurement path of a measurement cell using absorption spectroscopy of light emitted from broadband light sources via light guiding optics. The device is used among other things for measuring carbon monoxide (NO), carbon dioxide ($NO_2$), sulfur dioxide ($SO_2$), ozone ($O_3$), as well as components in fluid media and others, for combustion engines, especially in the online monitoring of diesel combustion engines, in environmental measurement technique, in medical technology, for instance for the measurement of respiratory air and others.

The determination of the concentration of substances using spectroscopic methods via broadband light sources and spectrally selective detectors, such as spectrometer of filtered optical detectors, is well known. Furthermore it is common to guide spectrally selective sources, such as Laser or filtered broadband light sources, via a measurement path to a filtered or unfiltered detector, to thereby characterize for instance gases or fluids. A logical conclusion of this is the utilization of LED-light sources, which are already spectrally limited, with and without optical filters. LEDs are to be understood here as broadband light sources, because in contrast to narrow line width sources (such as Laser) they emit a comparably broad frequency spectrum. The utilization of light guiding optics such as optical waveguides ("Lichtwellenleiter", LWL) for the purpose of mechanical and thermal decoupling or, respectively, for spatial separation of the measurement location from the source and receiving unit is also well known in the sensor technology.

The basic measurement principle of the optical spectroscopy is based on the measurement of the extinction of light that has passed a measurement cell. The inference to a defined substance concentration in the measurement cell is thus only an indirect method. Measurement reliability can be realized through the usage of additional so called reference wavelengths, whereby the spectral characteristic of the substance to be measured is utilized. These issues result for example in a measurement setup that is shown in FIG. 5 in the report of M. Degner and H. Ewald "Low cost sensor for online detection of harmful diesel combustion gases in UV-VIS region" [SPIE Photonics Europe 2006, Photonics in the Automobile 11, ISBN 0-8194-6254-3, F R Strasbourg, April 2006]. Next to broadband light sources, very often tuneable Laser sources are used in spectroscopy in order to reach high resolution. An absorption band of the requested substance is therein scanned with the Laser line. Herein, simply put, the intensity of the detected light outside the absorption band is to be viewed as a reference for the intensity at the place of the absorption band, because the light intensity is attenuated in the range of the absorption band.

The disadvantage herein is, that, although a high concentration resolution can be realized using the so-called laser spectroscopy, the number of detectable substances is limited due to the availability of adequate Laser light sources at the required interaction wavelengths of the substance. In addition, such arrangements often are cost intensive, less robust and therewith not suitable for mass production in the field of sensors.

The implementation of broadband light sources in combination with spectrometers likewise leads to cost intensive and in addition not very sensitive measurement arrangements. In this case the entire emission spectrum of the broadband light source is compared with the spectrum after the light has passed through the measurement cell. In contrast to this, filtered broadband light sources and especially LEDs are a more cost effective alternative. The general problem of arrangements with broadband light sources is the spectral and temporal fluctuation of the light intensity, or the emission characteristics, respectively, through which the resolution and especially the maximum reachable accuracy is strongly limited. In addition, high measurement times are required to reach such high resolutions because of the limited optical power density (except some very special LEDs).

Therefore the invention is based on the problem to provide a low cost, high resolution and at the same time fast spectroscopic method for the determination of the concentration of substances in gaseous or fluid media as well as a device for implementation of the method that is, respectively that are, robust against exterior influences.

The solution to this problem is obtained, according to the characterizing features of the method claim, in that the light emitted by the broadband light sources is guided partially through the measurement path of a self-referencing measurement cell to a measurement detector, and only partially through a reference path to a reference detector, wherein the measurement path and the reference path are partially identical, and the influences of the emission characteristics of the broadband light sources and of the mode weighing of the optical components are eliminated by way of mode couplers in the light paths. According to the characterizing features of the device claim the solution to this problem is obtained in that the light emitted by the broadband light sources via light guiding optics is guided through the measurement path of the self-referencing measurement cell, or only partially through a measurement cell to a measurement detector and partially via a reference path to a reference detector, and that for homogenizing the temporally and spatially varying emission characteristics of the broadband light sources a mode coupler is assigned to the light guide optics and to the light paths, respectively. The mode couplers should be dimensioned so as to have attenuation or scattering as low as possible. Typically, cost effective spectrally selective broadband light sources are used, whose light is guided via a light guiding system into the measurement path and is spectrally selectively evaluated.

One problem with commonly used beam splitters for spectroscopy is that the two partial beams cannot be held stable with sufficient accuracy relative to each other. This is caused by the time-varying local fluctuation of the emitted light intensity. The current distribution of the light is therein dependent from the current, time-varying inhomogeneous emission characteristic of the broadband light source. According to the invention the homogenization of the emission characteristic is realized by the use of the mode couplers. The subsequent splitting of the light is therefore no longer dependent on the fluctuating intensity distribution of the light source. The irradiated light basically "forgets" where it comes from. In principle scattering plates (milk glass, diffusor) can be used for this purpose, but a significant attenuation of light intensity would have to be expected. According to the invention the mode coupling is realized by way of the mode couplers inside the light guiding optics or, respectively, in the light paths. Optical waveguides are well suited for this purpose because mode couplers can be integrated therein. There are different design possibilities such as using very long fibers, tapers, multi-dimensional bending couplers etc. By using mode couplers, an efficient optical component for homogenizing the emission characteristic is utilized.

According to the invention, the remaining temporal fluctuations of the filtered broadband light sources, especially LEDs, are compensated by use of a suitable reference arrangement, i.e., the disturbances caused by the measurement arrangement and the surrounding are compensated with respect to the target value. Thus the measurement signal certainty is much bigger and especially through this, higher measurement accuracies/resolutions are achieved.

Due to the utilization of the mode couplers, realized for instance as ring couplers, and the fiber couplers for dividing the light, a source independent, robust and thus exact referencing is feasible, allowing to for instance measure gas concentrations below 1 ppm at a path length of some centimeters at a measurement time of some milliseconds. Furthermore the invention provides for another embodiment utilizing a self-referencing measurement arrangement so as to achieve the desired accuracy. Again, first the coupling and mode mixing of the individual light sources by way of fiber optics are used to achieve preferably the same path through the optical measurement cell for all wavelengths. Thus, disturbances, e.g., within the cell, affect the absorption and reference wavelengths in the same way. In contrast to the previously described measurement setup, light division and thereby a second receiving channel for referencing is omitted. Instead, the effective absorption path length of the measurement cell is varied (self-referencing) and therewith the measurement signal is modulated in a defined manner as it cannot be caused by disturbances. The signal sequence detected by the receiving unit can be demodulated correspondingly. By this means at least two signals are generated, that serve for referencing each individual wavelength. The advantage of this arrangement is that the entire optical path outside of the measurement cell is identical and is varied only within the measurement cell due to the modulation. Therefore only one receiving unit is required, there is no need for two identical receivers. Thus reception disturbances influence the reference signal and the measurement signal in the same way. The disadvantage here is the higher complexity of the measurement cell design.

In an exemplary arrangement, the path length through the medium to be measured can be varied by active switching or inclining or rotating of a glass platelet within the measurement cell, and thus a reference can be realized through the measurement volume. Through the possible usage of a concave mirror as a reflector also wavelength dependent dispersive disturbance effects are minimized.

In a further exemplary arrangement of the self-referencing measurement cell, a part of the light is reflected directly to the receiver at a first mirror. A second part is transmitted and reflected to the receiver at a second mirror in dependency of the orientation of a rotor. This rotor is propelled for instance by the flow of the medium to be measured and thereby modulates the effective path length. Also here there is a significant advantage compared to conventional reference arrangements due to the forming of the reference within the measurement cell, thus providing that disturbances act on the reference path and measurement path in the same way, so that a strong suppression of disturbances is realized.

Especially for gaseous media a further kind of referencing can be realized, through transferring the indirect measurement principle of the optical spectroscopy into a different, direct, sensor effect. Through an additional modulation of the measurement quantity, for instance through variation of pressure, the volume concentration of the gases is varied and therewith the detected extinction measurement values of the individual sources. If the variation of this additional physical effect is captured synchronously, for instance through the use of a conventional sensor (e.g. pressure), the effect of the modulation can be used to reference the whole system very accurately. This way, disturbances are suppressed and the real concentration values at normal pressure are obtained. Since pressure fluctuations are inherent in many systems, this is a very simple and effective method for self-referencing of a measurement cell. As one example of the above described methods for referencing and for the realization of low cost, precise spectroscopic sensors, the exhaust gas sensor for combustion processes or, respectively, —engines on the basis of novel UV-LEDs is mentioned here. This sensor is also constructively suited and proven for the usage in extremely rough environment, such as the exhaust channel of a car (amongst others high temperature, vibration, chemical aggressive media).

Figure 2:
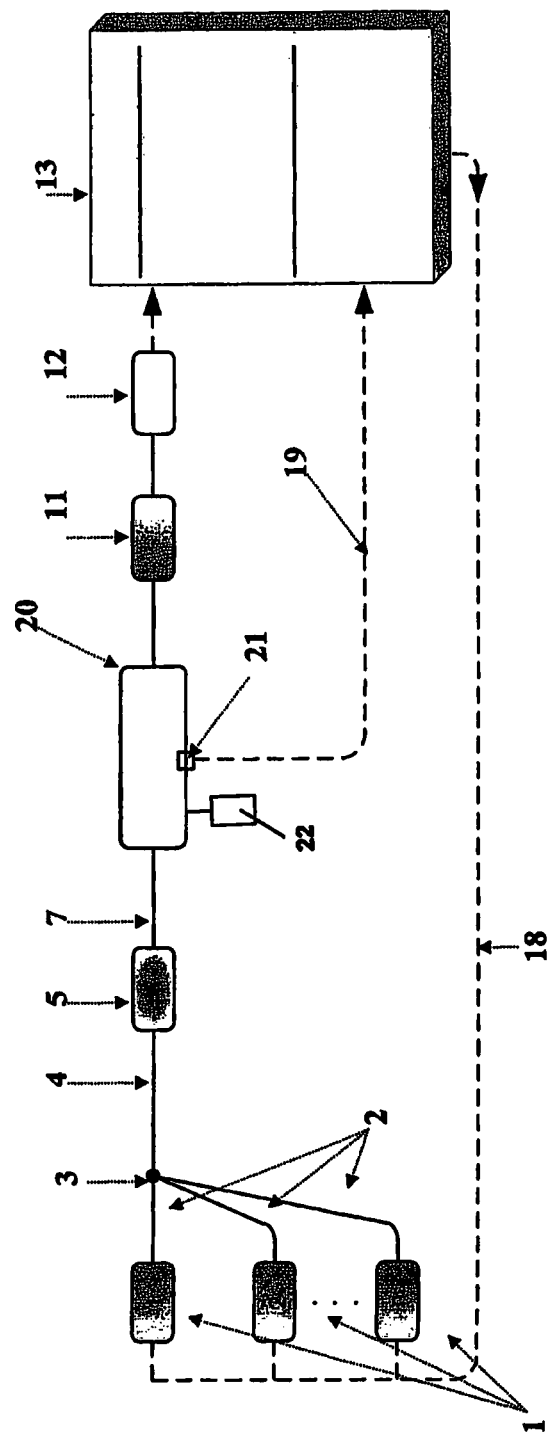
Figure 3:
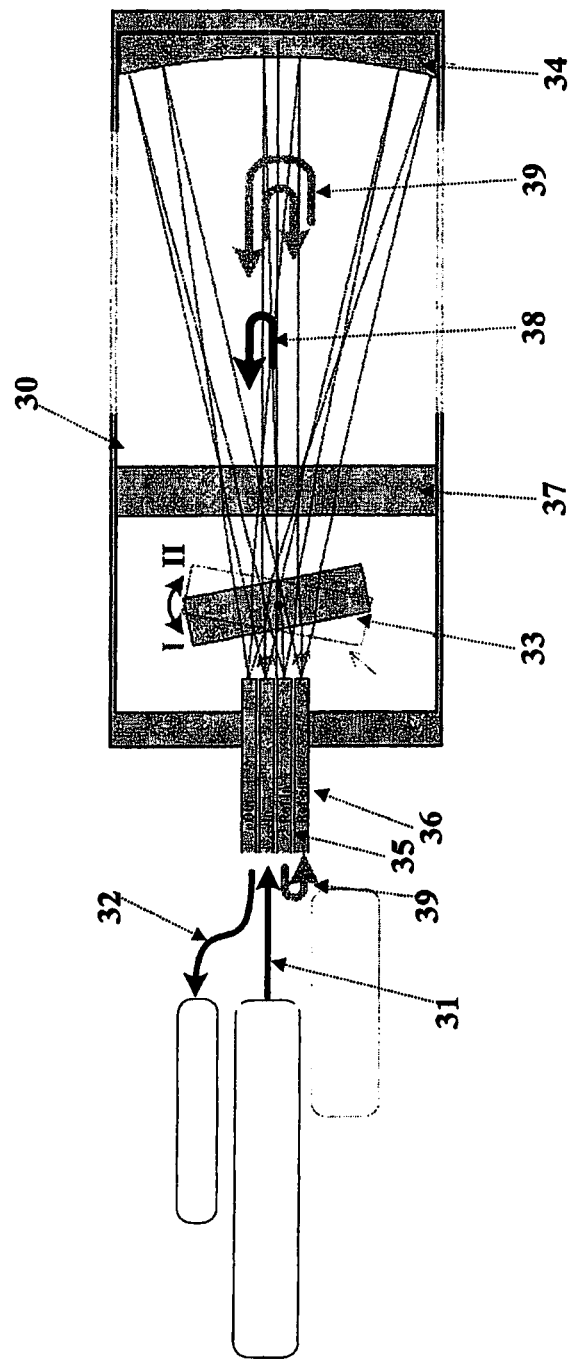
Figure 4:
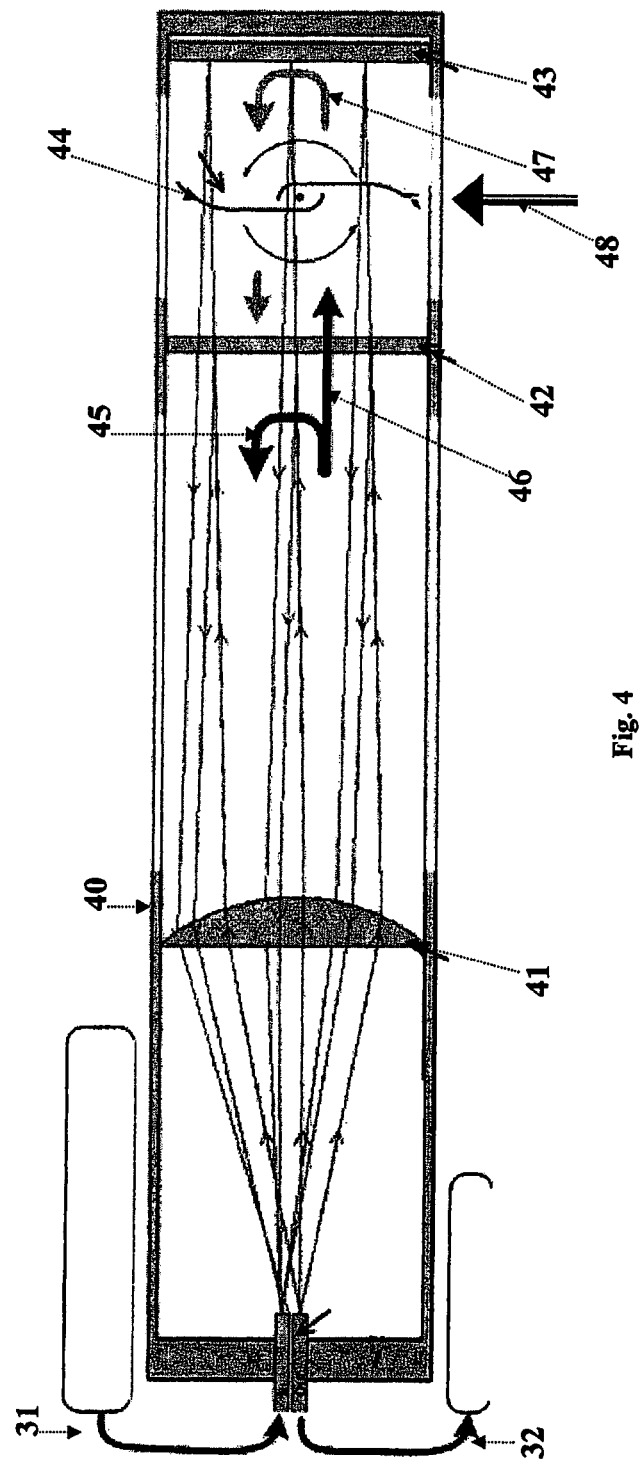

The device for measuring of substance concentrations in gaseous or fluid media according the invention is explained in detail in the following with the help of embodiments shown in the drawings. It is shown:

FIG. 1: a basic presentation of the first embodiment,

FIG. 2: a basic presentation of the second and third embodiment,

FIG. 3: a basic longitudinal section through a self-referencing measurement cell according to the second embodiment shown in FIG. 2 using a inclining glass platelet and FIG. 4: a basic longitudinal section through a second self-referencing measurement cell according the second embodiment shown in FIG. 2.

The first embodiment of a device for measurement of substance concentration in media shown in FIG. 1 includes 1 . . . n spectrally selective broadband light sources 1, for instance LEDs, whose light is guided via light waveguides 2 to a first fiber coupler 3, mixed therein and coupled to a light path. A waveguide 4 connected to the first coupler 3 is connected to a second fiber coupler 6 (e.g. 75/25) via a mode coupler 5. From this proceed two further waveguides 7 and 8, of which the waveguide 7 leads to a measurement cell 10 that contains the measurement media via a mode coupler 9, further to a first photo detector 11, to an ND-converter 12 and then to a controller 13, e.g. to a μC or a DSP. The second waveguide 8 leads the light of the source via a mode coupler 14 to a second photo detector 15, an ND-converter 16 and then to the above-mentioned controller. A fiber optical referencing is realized through appropriate signal analysis, e.g., a referencing by means of comparison of the two receiving channels. Thus a very precise concentration measurement of the substances within the measurement path of the measurement cell 10 is realizable. The electronic control of the spectrally selective light sources is done by means of the above-mentioned controller via the control line 18, which is advantages for a synchronous control and signal acquisition at high measurement rates.

According the invention the homogenization of the emission characteristics of the 1 . . . n spectrally selective light sources 1 is achieved through the utilization of the mode couplers 5, 9, 14. The subsequent splitting of the light is thus independent of the fluctuating intensity distribution of the light sources 1. The irradiated light basically "forgets" about where it comes from. Herein, the mode coupling is implemented by means of the mode couplers 5, 9, 14 within the optical waveguides 2, 4, 7, 8. There are different design possibilities for this purpose, such as the use of very long fibers, tapers, multi-dimensional bend couplers and others. With the mode couplers 5, 9, 14 an efficient optical component for the homogenization of the emission characteristics is used.

The fluctuations of the filtered spectrally selective broadband light sources 1 . . . n, especially LEDs, are compensated with the help of the reference arrangement, consisting of the light path of the waveguide 8, with mode coupler 14 and the second photo detector 15 as well as the associated ND-converter 16 with corresponding signal processing in the controller 13. Disturbances from the measurement arrangement and the surrounding are therewith suppressed with respect to the target quantity. Therefore the measurement signal reliability is substantially higher and for this reason in particular better measurement precision and resolutions are achieved. By using of mode couplers 5, 9, 14, implemented, e.g., as ring couplers, and the fiber couplers 3, 6 for splitting the light, a source-independent, robust and therefore exact referencing is feasible, in order to enable for example the measurement of gas concentrations of less than 1 ppm with an absorption path length of few centimeters at a measuring time of a few milliseconds.

The second embodiment shown in FIG. 2 includes, in the same way as the first embodiment shown in FIG. 1, the 1 . . . n spectrally selective broadband light sources 1, the optical waveguides 2, the fiber coupler 3, the mode coupler 5, the optical waveguides 4, 7, the measurement cell 20 including the measuring path, the photo detector 11, the ND-converter 12 and the controller 13. In contrast to the first embodiment according to FIG. 1, the fiber optical splitting of the light with the reference path is missing here.

In this case the measurement 20 cell is designed self-referencing. For this purpose, the light path is modulated for instance according to the representations in FIG. 3 or FIG. 4, respectively, or according to the third embodiment. For the purpose of detection of the last mentioned kind of modulation, sensor 21 is integrated into measurement line 19 and sends measurement values to the controller in the same way as the photo detector. A corresponding demodulation of the measurement signals is realized within the controller, the results of which are used for the referencing.

In this way, and in order to achieve source independence and thus the desired precision, a self-referencing measurement cell arrangement is realized in the second embodiment according to FIG. 2. Again, the coupling within the fiber coupler 3 and the mode mixing of the individual light sources 1 utilizing fiber optics in the mode coupler 5 are used to achieve nearly the same optical path through the measurement cell 20 for all wavelengths. With this, disturbances, for instance within the measurement cell 20, affect the absorption wavelengths and the reference wavelengths in the same way.

Here, in contrast to the first embodiment according to FIG. 1, light splitting and a second receiving channel for referencing are omitted. This is replaced by varying the effective absorption path length of the measurement cell (self-referencing) and thereby modulating the measurement signal in a well-defined way, as cannot be affected by disturbances. The signal sequence detected by the receiving unit can be demodulated correspondingly. By this, at least two signals are generated that are utilized for the referencing of each individual wavelength. The advantage of this arrangement is that the whole optical path outside the measurement cell 20 is identical and it is only varied within the measurement cell 20 through modulation. Therefore only one receiving unit is required, and there is no need for two identical receivers. Therefore, receiving disturbances will affect the reference signal and the measurement signal in the same way. The disadvantage here is the higher complexity of the design of measurement cell 30, 40.

Especially for gaseous media a further kind of referencing can be realized, through transferring the indirect measurement principle of the optical spectroscopy into another, direct, sensor effect, by using a simple measurement cell as it is described in the application example 1. This is done through additional modulation of the measurement quantity, for instance through variation of pressure, thereby varying the volume concentration of the gas and therewith the detected extinction measurement values of the individual sources. If the variation of this additional physical effect is synchronously detected, for instance using conventional sensors 21 (e.g. pressure), then the effect of this modulation can be used to reference the whole system very accurately, disturbances are thereby suppressed and the real concentration measurement values at normal pressure are determined. Since pressure fluctuations are inherent in many systems, this is a very simple and effective method for self-referencing of a measurement cell. Alternatively, the pressure inside the measurement cell can be varied using a pressure actuator 22.

The further embodiment according to FIG. 3 shows the measurement cell 30, wherein the substances to be measured are located, with inlets and outlets 31, 32 for the light emitted by the light sources 1, which is guided via optical waveguide 4 and mode coupler 5, measurement cell 30, and optical waveguide 7 to the photo detector 11. Within the measurement cell 30 a glass plate or, respectively, a glass platelet 33 is integrated, which is used for switching/varying the effective path length through the medium to be measured inside the measurement cell 30 through inclining or rotating. In position II of the glass platelet 33, the light passes along the path shown by the arrow 38. In the position I of the glass platelet 33, the light moves along the arrows 39 and additionally through the inlets and outlets 35, 36. Thus a reference is realised through interaction with the medium inside the measurement volume of the measurement cell 30. Advantageously, the light has passed the same optical components on both ways, i.e., in both positions I and II. Through the usage of a concave mirror 34 as a reflector at the right side of the measurement cell 30 (FIG. 3) wavelength dependent dispersive disturbances are minimized. A planar mirror could be used here as well. However, in this case the optional glass plate 37 limiting the measurement volume would be replaced by a collimator lens.

In the embodiment according to FIG. 4 of the self-referencing measurement cell 40, one part of the light coupled in via inlet 31 and collimated in the collimator lens 41 is reflected into direction 45 at the semitransparent mirror 42. This reflected light passes the collimating lens 41 once again and is guided to the outlet 32 and finally to the receiving unit 11, 12, 13. A second part of the light coupled in passes the semitransparent mirror 42 in the direction 46 and reaches the second measurement volume II. In dependency of the orientation of a rotor 44 inside the optical path, this part of the light is reflected at a fully reflecting mirror 43 (on the right in FIG. 4) and reaches the outlet 32 and, respectively, the receiving unit 11, 12, 13 through reflection 47.

The rotor 44 is propelled for instance by the flow of the medium to be measured which is passing the measurement cell 40 in the measurement volume II in the direction of the arrows 48. The blades of the rotor 44 serve to block light transmission, and therewith to modulate the effective path length of the light or, respectively, the interaction strength of the light with the media. The measurement volumes I and II of the measurement cell 40 contain the same medium to be measured.

As one application example of the above described methods for referencing and for the realization of low cost, highly precise spectroscopic sensors, the exhaust gas sensor for combustion processes or, respectively, combustion engines on the basis of novel UV-LEDs shall be mentioned here. This sensor is also constructively suited and proven for the usage in extremely rough environment, such as the exhaust channel of a car (amongst others high temperature, vibration, chemically aggressive media).

LIST OF REFERENCE NUMBERS

1 Light source
2 Optical waveguide
3 Fiber coupler
4 Optical waveguide
5 Mode coupler
6 Fiber coupler
7 Optical waveguide
8 Optical waveguide
9 Mode coupler
10 Measurement cell
11 Photo detector
12 Analogue/digital converter (ND converter)
13 Controller
14 Mode coupler
15 Photo detector
16 ND converter
18 Source controlling path
19 Measurement path
20 Referencing measurement cell
21 Sensor
22 Pressure actuator
30 Measurement cell
31 Light inlet of unstabilized light source respectively disturbed inlet path
32 Light outlet to the photo detector
33 glass platelet
34 Concave mirror as reflector
35 Inlet for light back coupling
36 Outlet of light back coupling
37 Optional glass plate
38 Direction of the first light path
39 Direction of the second light path
40 Measurement cell
41 Collimating lens
42 Half transparent mirror
43 Full mirror
44 Rotor
45 Direction of the first part of the light
46 Direction of the second part of the light
47 Reflection of the second light part
48 Direction of media flow

What is claimed is:

1. A method for determining the concentration of substance(s) in a gaseous or fluid medium within a measurement path of a measurement cell by referenced optical absorption spectroscopy with light emitted by one or multiple optical waveguide coupled LED light source(s) having time-varying local fluctuations of the emitted light intensity, said method containing the steps of:
    a) emitting light from the one or multiple optical waveguide coupled LED light source(s) and guiding the emitted light through one or multiple optical waveguide(s) coupled to the LED light source(s), and, if emitting light from multiple LED light sources and guiding the emitted light through multiple optical waveguides coupled to said LED light sources, combining the emitted light from the individual LED light sources into one optical waveguide using one or multiple wave guide coupler(s),
    b) homogenizing the light using one or multiple mode coupler(s) integrated into or coupled with one or multiple optical waveguide(s),
    c) guiding the homogenized light through the measurement path of the measurement cell containing the gaseous or fluid medium containing the substance(s) whose concentration is to be measured,
    d) after having passed the measurement cell, guiding the light through a further optical waveguide and mode coupler for further homogenization to a first photo detector to generate a measurement signal,
    e) generating a reference signal using the homogenized light of step b), wherein the reference signal is generated using one of
        i) branching off a part of the homogenized light into at least one optical waveguide branching off of the optical waveguide upstream of the measurement cell and guiding the branched off part of the homogenized light through the optical waveguide and one or multiple further mode coupler(s) for further homogenization to a second photo detector to generate the reference signal, or
        ii) modulating the amount of interaction of the homogenized light guided through the measurement cell with the substance(s) to be measured contained therein by varying an effective path length of the light through the measurement cell or by using and detecting pressure fluctuations of the medium inside the measurement cell, wherein the first photo detector generates the reference signal under altered measurement conditions with respect to the measurement signal,
    and
    f) determining the concentration of the substance(s) to be measured in the gaseous or fluid medium by comparing the measurement signal obtained in step d) with the reference signal obtained in step e).

2. The method according to claim 1, wherein variation of the effective path length or the pressure is taken into account in determining the concentration of the substance(s) to be measured.

3. The method of claim 1, wherein the amount of interaction of the homogenized light guided through the measurement cell with the substance(s) to be measured contained therein is varied in step e) ii) by switching between two discrete light paths of different lengths through the measurement cell.

4. The method of claim 1, wherein the amount of interaction of the homogenized light guided through the measurement cell with the substance(s) to be measured contained therein is varied in step e) ii) by dividing the measurement cell into a first compartment having a first length and a second compartment having a second length using a semitransparent mirror, wherein the first compartment defines a first path length through the measurement cell having double the first length, wherein the first compartment and the second compartment together define a second path length through the measurement cell having double the length of the sum of the first and second lengths by having a fully reflective mirror located opposite to the semitransparent mirror, the fully reflective mirror reflecting light having passed the semitransparent mirror back through the semitransparent mirror into the first compartment, so that a first part of the homogenized light passes through the measurement chamber along a path having the first path length and, simultaneously, a second part of the homogenized light passes through the measurement chamber along a path having the second path length, wherein the second part of the homogenized light is varyingly blocked or let through using a movable member in the second compartment.

5. The method of claim 1, wherein the amount of interaction of the homogenized light guided through the measurement cell with the substance(s) to be measured contained therein is varied in step e) ii) by using pressure fluctuations inside the medium inside the measurement cell or by actively varying the pressure of the medium inside the measurement cell.

6. The method of claim 1, wherein multiple optical waveguide coupled LED light sources of different wavelengths are used for the determination of concentrations of multiple substances in the gaseous or fluid medium inside the measurement cell, wherein the wavelengths of the individual light sources are chosen to overlap with absorption bands of the substances to be measured.

7. The method of claim 6, wherein at least one further optical waveguide coupled LED light source has a wavelength corresponding to a reference wavelength chosen to have little or no overlap with absorption bands of the substances to be measured.

8. A device for determining the concentration of substance(s) in a gaseous or fluid medium within a measurement path of a measurement cell by referenced optical absorption spectroscopy with light emitted by one or multiple optical waveguide coupled LED light source(s) having time-varying local fluctuations of the emitted light intensity, said device comprising
one or multiple optical waveguide coupled LED light source(s) which emit light coupled with one or multiple optical waveguide(s) guiding the emitted light,
one or multiple wave guide coupler(s), where, if multiple optical waveguide coupled LED light sources are present, the multiple LED light sources emit light guided by multiple optical waveguides coupled to said LED light sources, for combining the emitted light from the individual LED light sources into one optical waveguide,
one or multiple mode coupler(s) integrated into or coupled with one or multiple optical waveguide(s) for homogenizing the emitted light,
a measurement cell containing the gaseous or fluid medium containing the substance(s) whose concentration is to be measured, wherein the measurement cell defines a measurement path for the homogenized light and is optically connected to an optical waveguide guiding homogenized light into the measurement cell along the measurement path,
a further optical waveguide receiving the light at an end of the measurement path through the measurement cell, leading to a further mode coupler for further homogenization, and
a first photo detector connected to the further optical waveguide for receiving the light coming out of the measurement cell after further mode coupler homogenization, wherein the first photo detector is configured to generate a measurement signal,
a reference signal generator that generates a reference signal using the homogenized light of the LED light source(s), comprising one of
i) a branch optical waveguide coupled to the optical waveguide leading to the measurement chamber by means of a waveguide coupler upstream of the measurement cell, the branch optical waveguide leading to one or multiple further mode coupler(s) for further homogenization and to a second photo detector configured to generate the reference signal, or
ii) a modulator configured to modulate the amount of interaction of the homogenized light guided through the measurement cell with the substance(s) to be measured contained therein, said modulator comprising a means for varying an effective path length of the homogenized light through the measurement cell or a pressure sensor for detecting pressure fluctuations of the medium inside the measurement cell, wherein the first photo detector is configured to generate the reference signal under altered measurement conditions with respect to the measurement signal,
and
a controller configured to receive the measurement signal and the reference signal, and to determine the concentration of the substance(s) to be measured in the gaseous or fluid medium by comparing the measurement signal with the reference signal.

9. The device of claim 8, wherein the means for varying an effective path length of the homogenized light through the measurement cell is a glass platelet located inside the measurement path inside the measurement cell which is tiltable or rotatable between a first position and a second position, wherein in the first position the light path is directed to a reflecting mirror such that homogenized light coupled into the measurement cell is coupled out after one reflection at the reflecting mirror and then guided towards the first photo detector, and wherein in the second position, the homogenized light is deflected by the platelet such that it is coupled out into an intermediate optical waveguide and reintroduced into the measurement cell, reflected at the reflective mirror for a second time and then coupled out and guided towards the first photo detector.

10. The device of claim 8, wherein the means for varying an effective path length of the homogenized light comprise a semitransparent mirror dividing the measurement cell into a first compartment having a first length and a second compartment having a second length, wherein the second compartment comprises a fully reflective mirror located opposite to the semitransparent mirror, wherein the first compartment defines a first path length through the measurement cell having double the first length and wherein the first compartment and the second compartment together define a second path length through the measurement cell having double the length of the sum of the first and second lengths, further comprising a movable member located in the second compartment and configured to varyingly block or let through the homogenized light passing through the second compartment.

11. The device of claim 10, wherein the movable member is a rotor.

12. The device of claim 11, wherein the rotor is propelled by a stream of the medium through the measurement cell.

13. The device of claim 8, further comprising a pressure actuator for varying the pressure of the medium inside the measurement cell.

* * * * *